United States Patent [19]
Sittler

[11] Patent Number: 5,482,678
[45] Date of Patent: Jan. 9, 1996

[54] ORGANIC CHEMICAL SENSOR

[75] Inventor: Fred C. Sittler, Victoria, Minn.

[73] Assignee: Rosemount Inc., Eden Prairie, Minn.

[21] Appl. No.: 337,135

[22] Filed: Nov. 10, 1994

Related U.S. Application Data

[63] Continuation of Ser. No. 66,980, May 25, 1993, abandoned.

[51] Int. Cl.$^6$ .............................. G01N 19/10; G01B 7/16; G01M 3/04
[52] U.S. Cl. .................. 422/90; 73/24.06; 422/68.1; 422/82.01; 422/82.02; 422/94; 422/98; 436/72; 436/139; 436/149; 436/151
[58] Field of Search ................................ 73/24.06, 31.05, 73/31.06, 775–776, 778, 579; 338/2–5, 34–35; 422/68.1, 82.01, 82.02, 83, 90, 94, 98; 436/72, 139, 149, 151

[56] References Cited

U.S. PATENT DOCUMENTS

| | | | |
|---|---|---|---|
| 2,553,986 | 5/1951 | Statham | 73/775 X |
| 2,558,563 | 6/1951 | Janssen | 73/775 X |

(List continued on next page.)

FOREIGN PATENT DOCUMENTS

| | | |
|---|---|---|
| WO86/07483 | 12/1986 | European Pat. Off. . |
| 2710847A1 | 9/1978 | Germany . |
| 3724384C1 | 4/1988 | Germany . |
| 59-67445 | 4/1984 | Japan . |
| 63-78049 | 4/1988 | Japan . |
| 63-100353 | 5/1988 | Japan . |
| 63-100352 | 5/1988 | Japan . |
| 2-212745 | 8/1990 | Japan . |
| 2-269912 | 11/1990 | Japan . |
| 2-311749 | 12/1990 | Japan . |
| 3-21850 | 1/1991 | Japan . |
| 3-21849 | 1/1991 | Japan . |
| 3-28741 | 2/1991 | Japan . |
| 3096846 | 4/1991 | Japan ..................................... 73/23.2 |
| 3-111751 | 5/1991 | Japan . |
| 3-111750 | 5/1991 | Japan . |
| 3-226649 | 10/1991 | Japan . |
| 4-168354 | 6/1992 | Japan . |
| 1355176 | 2/1973 | United Kingdom . |

OTHER PUBLICATIONS

Article entitled "Micromechanical Threshold Temperature Sensor", by K. E. Petersen, published in *IBM Technical Disclosure Bulletin, vol. 21, No. 3, Aug. 1978*, p. 1204.

Article entitled "Substrate Dimensional Changes Upon Adsorption: Methane, Xenon and Krypton Adsorbed on Graphite", published in *Surface Science 92 (1980)*, pp. 453–466.

*Primary Examiner*—James C. Housel
*Assistant Examiner*—Arlen Soderquist
*Attorney, Agent, or Firm*—Westman, Champlin & Kelly

[57] ABSTRACT

In this invention, a first sensor senses an organic gas, liquid or vapor and includes a first support having a first support surface with a layer of material fastened to it. In the presence of liquid, gas or vapor, the material swells and expands so as to vary at least one of its dimensions. Such expansion develops a stress at an interface between the first support surface and the material, and strain sensitive resistors detect the stress and produce an output which varies as a function of the stress at the interface. One of a pair of piezoresistors is located where there is increased stress and the other piezoresistor is disposed where there is reduced stress. If desired, a second sensor similar in structure to the first but exposed only to a reference organic liquid, gas or vapor temperature compensates the first. In another embodiment of the invention, an organic chemical responsive sensor includes a first support having a first support surface and a first capacitor plate fastened to the first support. A second support coupled to the first support spaces a second capacitor plate a distance away from the first plate. A material which expands in the presence of organic liquid, gas or vapor is applied to the first support surface so that upon expansion, the first support deflects and changes the distance between the two capacitor plates, thereby changing an electrical capacity between the plates. Another sensor of similar structure may optionally temperature compensate the first.

7 Claims, 5 Drawing Sheets

U.S. PATENT DOCUMENTS

| | | | |
|---|---|---|---|
| 2,589,983 | 3/1952 | Blodgett et al. | 338/35 X |
| 2,933,665 | 4/1960 | Dimeff | 73/775 X |
| 2,990,529 | 6/1961 | Courtney-Pratt | 73/775 X |
| 3,088,323 | 5/1963 | Welkowitz et al. | 73/775 X |
| 3,137,834 | 7/1964 | Pfann | 73/775 X |
| 3,440,881 | 4/1969 | Thoma | 73/337.5 |
| 3,460,378 | 8/1969 | Gepollina | 73/775 X |
| 3,461,723 | 8/1969 | Thoma | 73/335 |
| 3,534,608 | 10/1970 | Thoma et al. | 73/337.5 |
| 3,582,728 | 6/1971 | Thoma | 317/246 |
| 3,654,576 | 4/1972 | Kurtz et al. | 338/2 |
| 3,705,993 | 12/1972 | Grigorivici et al. | 73/776 X |
| 3,802,268 | 4/1974 | Thoma | 73/336.5 |
| 3,970,982 | 7/1976 | Kurtz et al. | 338/4 |
| 3,993,150 | 11/1976 | Brosh et al. | 177/211 |
| 4,051,451 | 9/1977 | Kurtz et al. | 338/4 X |
| 4,058,802 | 11/1977 | Meyers | 340/224 |
| 4,224,595 | 9/1980 | Dolan | 338/34 |
| 4,237,721 | 12/1980 | Dolan | 73/23 |
| 4,265,117 | 5/1981 | Thoma et al. | 73/359 |
| 4,327,359 | 4/1982 | Kurtz | 73/579 X |
| 4,343,768 | 8/1982 | Kimura | 422/98 X |
| 4,406,992 | 9/1983 | Kurtz et al. | 338/2 |
| 4,456,901 | 6/1984 | Kurtz et al. | 338/4 |
| 4,508,598 | 4/1985 | Giner | 204/1 |
| 4,510,671 | 4/1985 | Kurtz et al. | 338/4 X |
| 4,516,430 | 5/1985 | Kurtz et al. | 338/4 X |
| 4,561,286 | 12/1985 | Sekler et al. | 73/24.06 |
| 4,572,900 | 2/1986 | Wohltjen | 422/98 X |
| 4,631,952 | 12/1986 | Donaghey | 73/23 |
| 4,649,364 | 3/1987 | Tamahashi et al. | 338/35 X |
| 4,729,824 | 3/1988 | Giner | 204/415 |
| 4,855,706 | 8/1989 | Hauptly | 338/34 |
| 4,899,125 | 2/1990 | Kurtz | 338/3 X |
| 4,909,078 | 3/1990 | Sittler et al. | 73/204.26 |
| 4,928,513 | 5/1990 | Sugihara et al. | 338/35 X |
| 4,932,247 | 6/1990 | Görres | 73/129 |
| 4,944,187 | 7/1990 | Frick et al. | 73/718 |
| 4,965,698 | 10/1990 | Thoma et al. | 361/286 |
| 5,028,394 | 7/1991 | Lowell, Jr. et al. | 73/24.06 X |
| 5,048,336 | 9/1991 | Sugihara et al. | 338/35 X |
| 5,079,944 | 1/1992 | Boenning et al. | 73/23.4 |
| 5,086,286 | 2/1992 | Yasukawa et al. | 338/34 |
| 5,090,254 | 2/1992 | Guckel et al. | 73/778 X |
| 5,099,437 | 3/1992 | Weber | 364/550 |
| 5,101,657 | 4/1992 | Lahlouh et al. | 73/40.5 |
| 5,150,603 | 9/1992 | Boenning et al. | 73/31.05 |
| 5,192,938 | 3/1993 | Ort | 73/776 X |

ORGANIC CHEMICAL SENSOR

This is a Continuation of application Ser. No. 08/066,980, filed May 25, 1993, now abandoned.

BACKGROUND OF THE INVENTION

This invention relates to gas, liquid and vapor sensors and more particularly, to such sensors which use a swellable member as the means for sensing the gas, liquid or vapor.

There is a desire to reduce emissions of organic chemicals in the process control and other industries. Refineries and intermediate users such as pumping stations and storage facilities emit large amounts of undesired organic chemicals. Progressively more stringent government regulations have addressed this problem, most notably the U.S. federal regulations 37 CFR 191–192 and regulations from other states as well. Such rules regulate emissions from "release points" and mandate monitoring for fittings, joints, packing glands, flanges, valves, pump seals, compressor seals, pressure relief seals, open-ended lines and sampling connections. Valves, because of their number and relatively high emission rates, are the major emission source. The U.S. Environmental Protection Agency (EPA) Office of Air Quality sets limits on emissions from various "release points", as published in "Protocols for Generating Unit-Specific Emission Estimate for Equipment Leaks of VOC and VHAP", EPA publication 450/3-88-010.

Organic chemical sensors formed of polymers, such as a room-temperature-vulcanized (RTV) silicones impregnated with electrically conductive particles to form a variable resistor are known. Exposure to organic chemicals swells or increases the volume of the polymer which moves the particles farther apart and increases electrical resistivity. Such sensors, however, can have poor stability and repeatability because the organic chemicals damage the particles. Also, where an "intrinsically safe" design is needed for explosive vapors, such sensors are unsuitable because they carry an electric current and may spark under fault conditions. Further, outputs from such sensors are typically low level and require a Wheatstone bridge circuit for sensing. The high impedance bridge signals are noisy and transmission over long distance requires extensive shielding and amplification.

There is thus a need for an inexpensive organic chemical sensor which has a more stable and repeatable output which can be used in the presence of explosive vapors and which are more suitable for transmission in a noisy process control environment.

SUMMARY OF THE INVENTION

In this invention, a first sensor senses an organic gas, liquid or vapor and includes a first support having a first support surface coated with a layer of material. In the presence of organic liquid, gas or vapor, the material expands so as to vary at least one of its dimensions. Such expansion develops a stress at an interface between the first support surface and the material, and strain sensitive resistors detect the stress and produce an output which varies as a function of the stress at the interface. One of a pair of piezoresistors is located where there is increased stress and the other piezoresistor is disposed where there is reduced stress. If desired, a second sensor similar in structure to the first but exposed only to a reference organic liquid, gas or vapor temperature-compensates the first sensor. In such a second sensor, the polymer expands as a function of temperature and stresses an interface between the polymer and a second support surface. Strain sensitive resistors responsive to the strain at the interface change resistance and thereby provide an output representative of temperature. In another embodiment, an organic chemical responsive sensor includes a first support having a first support surface and a first capacitor plate fastened to the first support. A second support coupled to the first support spaces a second capacitor plate a distance away from the first plate. A material which expands in the presence of organic liquid, gas or vapor is applied to the first support surface so that upon expansion, the first support deflects and changes the distance between the two capacitor plates, thereby changing an electrical capacity between the plates. If desired, another capacitive sensor similar in structure to the first but exposed only to a reference organic liquid, gas or vapor temperature compensates the first. In this sensor, the polymer expands as a function of temperature and deflects an upper capacitor plate downwards, so as to decrease the distance between two capacitor plates and thereby increase an electrical capacitance.

DETAILED DESCRIPTION OF THE PREFERRED EMBODIMENTS

Figure 1:
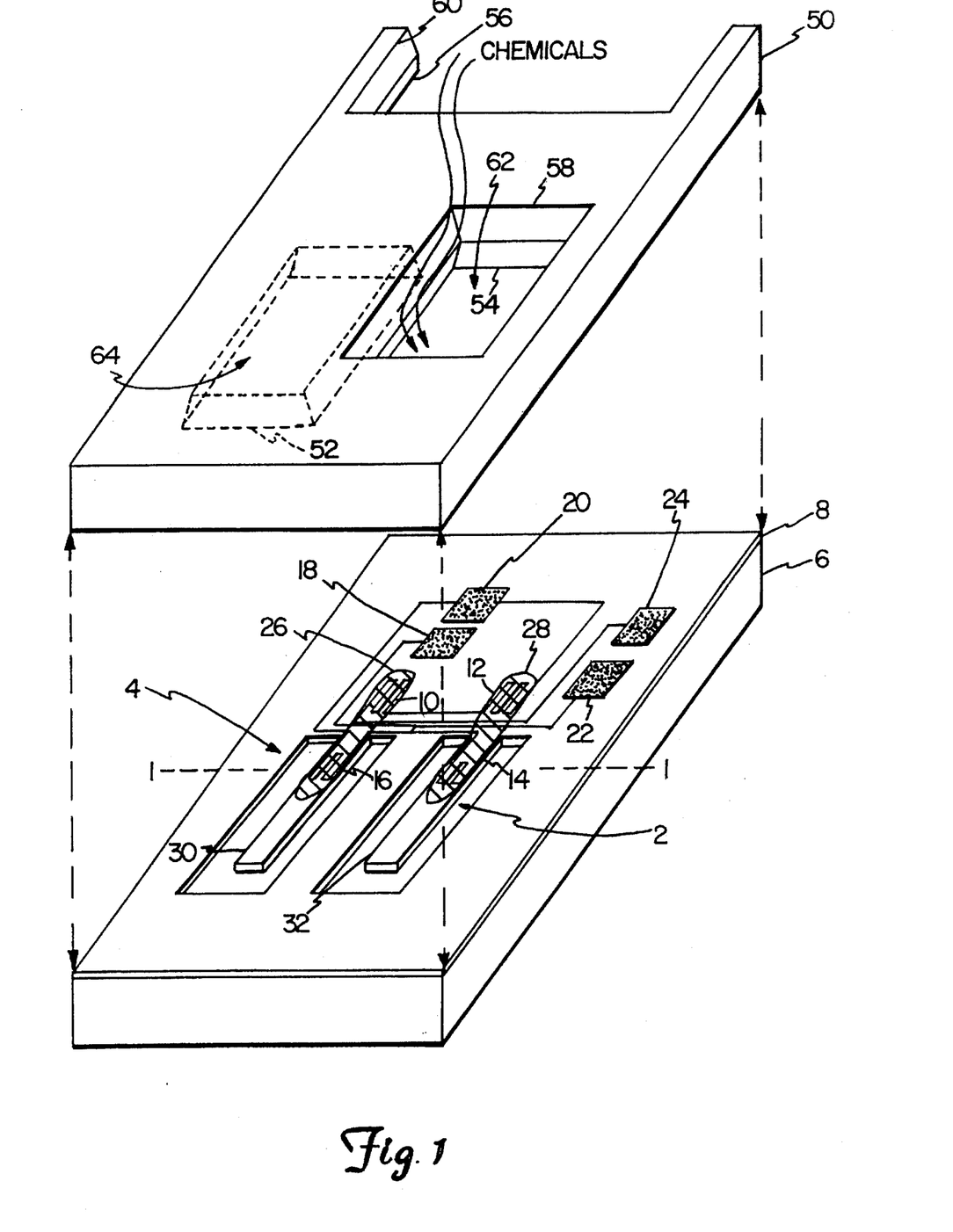
FIG. 1 is an exploded view of an embodiment of the present invention.

In FIG. 1, sensors 2,4 formed on a silicon substrate 6 sense or measure concentrations of liquid, gas or vapor organic chemicals. Sealed chamber 64 isolates sensor 4 from chemicals to provide a reference sensor output free of the effects of varying chemical concentrations. Window 62, however, exposes sensor 2 to organic chemicals so that its output varies as a function of organic chemical concentration. In sensor 2, a strip of polymer 28, which swells when exposed to organics, bonds to an underlying silicon nitride beam 32, which is dimensionally stable when exposed to organic chemicals. Substrate 6 rigidly supports one portion of beam 32, while a free portion of beam 32 is cantilevered over cavity 62 and free to flex. When polymer strip 28 receives chemical vapors, it swells while the nitride to which it is fastened does not. The resulting strain causes the free portion to bend or flex. A strain gauge resistor 14 senses strain in the free end of beam 32. In the rigid portion of the nitride strip, however, there is little strain and a strain gauge resistor 12 provides a reference signal free of strain.

In sensor 4, a strip of polymer 26 is exposed solely to a reference organic chemical gas, liquid or vapor. Alternatively, sensor 4 is sealed in a vacuum. Polymer 26 swells or expands in at least one dimension with temperature. A silicon nitride beam 30 on which polymer 26 rests, however, is insensitive to the organic chemicals and temperature and is dimensionally stable. Substrate 6 rigidly supports one portion of beam 30 while a free end is cantilevered over a cavity and free to deflect. A strain gauge resistor 16 deposited on beam 30 senses the strain induced by the deflection, while a strain gauge resistor 10 is located on substrate 6 in a position of substantially reduced stress. The resistance of resistors 10,16 is representative of the temperature responsive nature of polymer 26 and is used to compensate the output from organic chemical responsive strain gauges 12,14.

Figure 3:
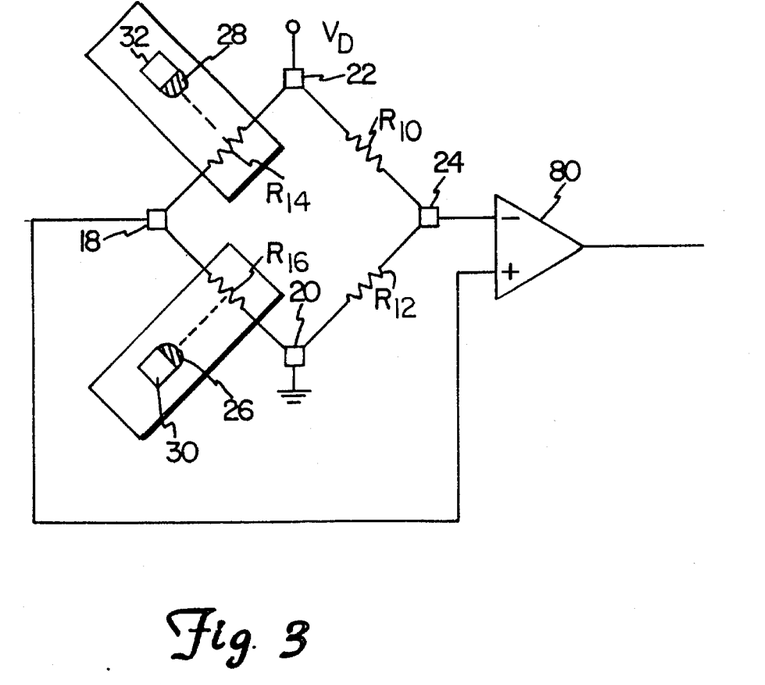
FIG. 3 is a schematic of a wheatstone bridge circuit embodying the present invention.

The four resistors $R_{10}$–$R_{16}$ are connected in a bridge circuit, as shown in FIG. 3. Each of the resistors $R_{10}$–$R_{16}$ correspond to the same numbered resistor in FIG. 1. For example, resistor $R_{10}$ corresponds to resistor 10 in FIG. 1. Pad 18 is connected to the non-inverting input on an op-amp 80, pad 20 is connected to a ground, pad 22 is connected to $V_D$ and pad 24 is connected to the inverting input on the op-amp. The variable reference resistor $R_{16}$ comprises beam 30 and polymer 26 while organic chemical sensing resistor $R_{14}$ comprises beam 32 and polymer 28. The output of op-amp 80 is a temperature compensated signal representative of the concentration of organic liquid, gas or vapor. Other well-known means for monitoring resistance change, such as comparators, sliding comparators and ohmmeters may also be used.

Sensors 2,4 are batch fabricated from average resistivity, double polished silicon wafers having a <100> crystal orientation, so as to facilitate uniform etching. A silicon nitride film 8 is deposited and two U-shaped openings are photoshaped in the nitride. Next, a doped and annealed conductive polysilicon film is deposited and photoshaped to provide resistors 10–16, pads 18–24 and associated interconnect. The polysilicon layer is overcoated with another nitride layer and contacts openings are cut over the pads to allow wirebonding, and to cut the two U-shaped openings back down to bare silicon. Resistor 14 is disposed on beam 32 at a position of increased stress when beam 32 deflects, and resistor 12 is on silicon substrate 6 at a location of reduced stress. Similarly, sensor 4 has resistor 16 located at an increased stress point and resistor 10 at a location having reduced stress. A contact metallization deposition and photoshape finishes bondable contacts 18–24. Two holes 66,68 (see FIG. 2) are next photoshaped in the nitride on the backside of the wafers corresponding to the area under the U-shaped openings. The hole openings must compensate for the 45° etching characteristic of <100> oriented silicon and therefore are slightly larger than the openings as shown in FIG. 1. A one micron thick polymeric layer is screen printed on the wafer to provide polymers 26,28. A silicon etch, without protecting either side of the wafer, subsequently removes all the silicon in the two U-shaped areas and leaves nitride beams 30,32 overhanging the two completely etched-out cavities. Alternatively, beams 30,32 may be made of another stiff material, such as silicon, silicon oxide or polysilicon, or layers of these materials, which exhibit substantially no hysteresis upon deflection.

Figure 2:
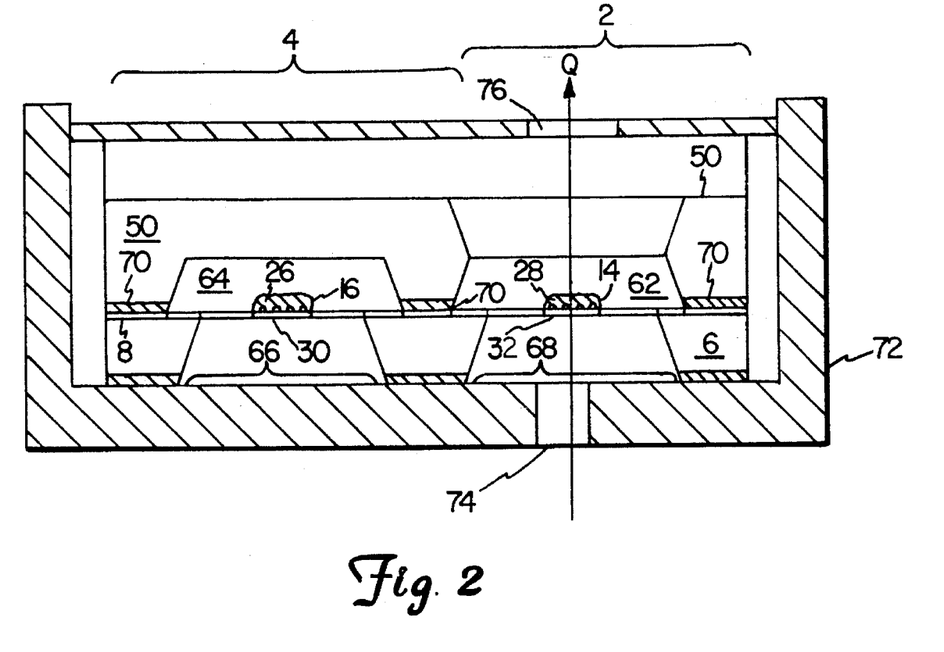
FIG. 2 is a cross section of an embodiment of the invention as viewed from line 1—1 in FIG. 1.

A second piece of silicon 50 is used to encapsulate sensor 4. Starting from the same silicon stock as for substrate 6, a nitride layer coats both sides of the cover wafer. Nitride openings 52,54,56 in the backside of the wafer are cut, and nitride openings 58,60 are subsequently aligned to backside openings 54,56 so that when the silicon etch is completed, a throughhole 62 is cut through silicon 50 and a cavity 64 is cut in the backside of the wafers. Cavity 64 is designed to cover sensor 4 and throughhole 62 fits over sensor 2, but allows complete access of organic liquid, gas or vapor to sensor 2. Substrates 6 and 50 are bonded together using an adhesive such as polyimide, re-flow TEFLON, a brand of polytetrafluoroethylene 70 or other methods known in the industry. The wafers are diced to obtain individual die and the die attached to a header 72 having an aligned pair of opening vents 74,76 oriented to facilitate liquid, gas or vapor flow through sensor 2. A binder fastens the die to header 72.

Polymers 26,28 are made from a swellable polymer such as RTV silicone polymer, synthetic rubber, polyvinyl chloride, polymethyl methacrylate, silicone, or a mixture of these cross-linked polymers which expand in the presence of an organic chemical. The polymers necessarily reacts more slowly to organics having a low vapor pressure than to ones with a high vapor pressure. The silicon RTV used in an embodiment of the present invention is sensitive enough to give a full scale response of 3 mV (with 10 V applied to the bridge) when 0.1 ml trichloroethane is inject into 4.5 liters of air. Cross-linked polymers absorb the gas, liquid or vapor of interest and consequently expand their dimensions. These materials are preferred because the dimensional expansion is reversible and substantially without hysteresis. In fact, shrinkage of the polymer after an exposure to an organic may be hastened by heating. RTV silicone polymer expands in the presence of many organics and is preferred because it is low cost, relatively non-toxic and easy to apply. Furthermore, RTV withstands the rigors of semiconductor processing better than other polymers. RTV responds to hydrocarbons, chlorohydrocarbons, fluorocarbons and silicarbons such as unleaded regular gasoline, leaded gasoline, diesel fuel, jet A fuel, toluene, n-xylene, methyl alcohol, n-hexane, cyclohexane, methylpentane, trichloroethylene, chloroform, dichloromethane, dichloroethylene, benzene, 2-methylpentane, methylcyclopentane; isooctane, n-heptane, ethylbenzene, butylbenzene, hexyl alcohol, isopropyl alcohol and octane.

Figure 4:
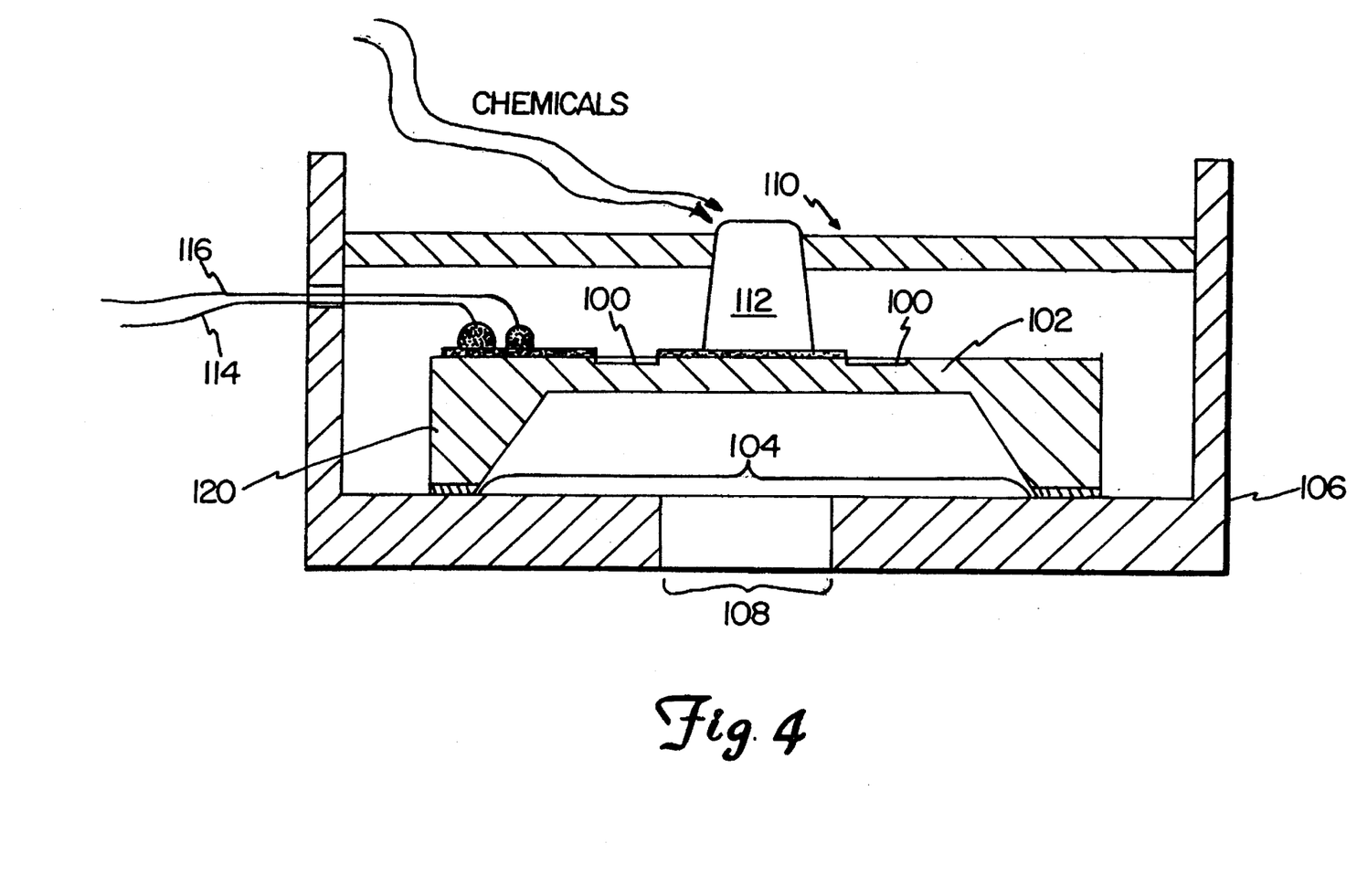
FIG. 4 is a cross sectional view of a second embodiment of the present invention.

In FIG. 4, a sensor die 120 set in header 106 senses concentrations of liquid, gas or vapor organic chemicals. In sensor die 120, a cylindrical piece of polymer 112 is restrained by a crossbar structure 110 in header 106. Polymer 112 swells and expands in the presence of organic chemicals so as to exert a force on a diaphragm 102 and deflect it. A set of piezoresistors 100 are positioned on diaphragm 102 in an area of increased stress and change their resistance as a function of the stress induced by the diaphragm deflection. The piezoresistors are connected in a bridge circuit (not shown), or another circuit designed to provide a change in output when the resistors change resistance.

Sensor die 120 is batch fabricated from nitride coated double polished silicon wafers. A polysilicon layer is deposited and photoshaped to provide resistors 100 and associated interconnect on the surface of the wafer. A contact metallization layer is deposited and photoshaped to provide bondable contacts. A subsequent nitride coating protects the frontside metallization while the backside is photoshaped to provide a diaphragm window 104. Window 104 is then etched out to provide diaphragm 102, after which contact openings are cut in the frontside nitride to facilitate bonding. After dicing and bonding two wires 114,116 to sensor die 120, it is affixed to header 106 and enough polymer 112 is introduced into header 106 through opening 110 to ensure intimate contact to the surface of diaphragm 102. The polymer piece should be positioned near the center of the diaphragm in a position where deflection is the greatest. A vent 108 in header 106 ensures that sensor die 120 is not responsive to pressure.

Figure 5:
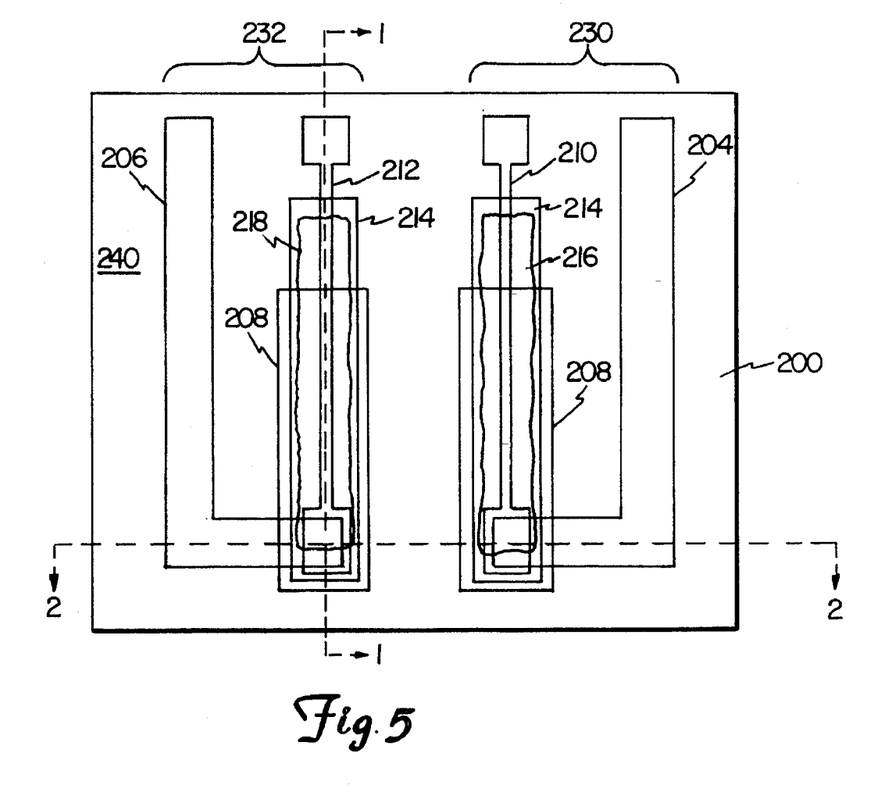
FIG. 5 is a plan view of a third embodiment of the present invention.
Figure 6:
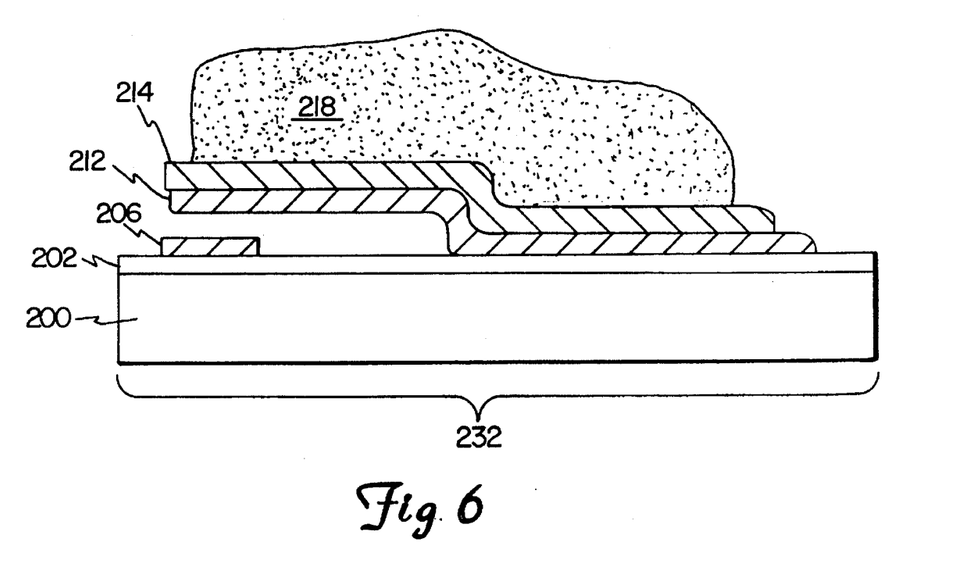
FIG. 6 is a cross section of the reference sensor taken as viewed from line 1—1 in FIG. 5, but with the cap removed.
Figure 7:
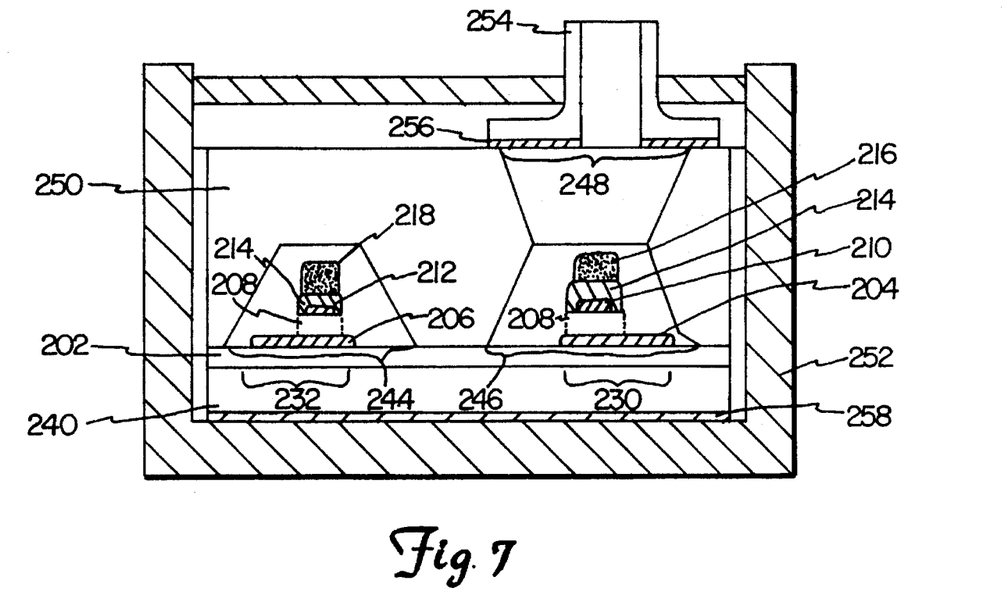
FIG. 7 is a cross section of an embodiment of the invention taken as viewed from line 2—2 in FIG. 5.

Additional sensors which monitor the dimensional changes of a polymer responsive to organic chemicals may be made with sensing means other than strain sensitive detection means. For example, optical detection means may be employed. In one embodiment, a mirror on a beam which deflects as a function of the stress induced by a organic responsive polymer may normally be focused on a first optical fiber and upon the deflection, be focused on a second optical fiber. Alternatively, the detection means can be capacitive. In FIGS. 5, 6 and 7, a silicon sensor die 240 containing two capacitive sensors 230,232 is shown, the former sensor for sensing organic liquid, gas or vapors and the latter for temperature compensating the other.

Sensor 230 has a bottom capacitor plate 204 and a top capacitor plate 210 cantilevered over the bottom plate. A polymer layer 216 responsive to organic liquid, gas or vapors is mechanically coupled to cantilevered plate 210, so that when the polymer expands, the plate deflects downward and the electrical capacity of the capacitor increases. Sensor 232 is similar in construction, but is exposed only to a reference organic liquid, gas or vapor. Sensor 232 has a lower capacitor plate 206 and a cantilevered upper plate 212 spaced a distance from the other plate. A polymer 218 is mechanically coupled to upper plate 212 so that when polymer 218 expands as a function of temperature, plate 212 deflects downward and an electrical capacity of sensor 232 increases.

A capacitance measuring circuit, such as the one described in U.S. Pat. No. 4,598,251 is connected to sensor 230, and output from sensor 232 compensates the output from sensor 230. Sensor 230 may also be connected to a circuit where the resistance between polysilicon layer 204, 210 is monitored. When polymer 216 expands so as to deflect polysilicon layer 210 downwards to contact polysilicon layer 204, the resistance is significantly reduced. This alternate type of sensor operates as a "make-break" sensor, where the presence of an organic liquid, gas or vapor is indicated by a low resistance output between the polysilicon layers but where the sensor has a high impedance output otherwise. The low power consumption of this arrangement is particularly advantageous in transmitters, since transmitters receive their operating power over the same two wires over which they communicate. Such arrangement is also preferred for a low cost application to indicate the mere presence of an organic liquid, gas or vapor, but where the knowledge concentration of the organic chemical is not necessary. An alternative "make-break" sensor having a similar structure to the first has a normally low impedance connection when isolated from organic gas, liquid or vapor, but which switches to a high impedance connection upon exposure to the organic.

Sensors 230,232 are batch fabricated using standard sensor fabrication techniques and have an insulating substrate 200, made of a material such as sapphire, coated with a layer of silicon nitride 202 or another insulating film. An insulating substrate like sapphire or alumina is preferred in order to simplify the sensor design, since a conductive substrate would have to be connected to a power supply to reduce capacitive coupling and to properly bias the substrate. A polysilicon layer is deposited and photoshaped to provide lower plates 204,206. A layer of silicon dioxide or some other easily etchable material is deposited and photoshaped atop the polysilicon, to provide oxide spacers 208. Layer 208 merely serves as a mechanical spacer during processing and is later removed by an buffered HF etching process to provide a gap between two plates of each capacitor. The sensitivity of the sensor may be adjusted by modifying the thickness of the oxide layer. Next a second polysilicon layer is deposited and photoshaped to provide upper capacitor plates 210,212. A nitride layer is deposited and photoshaped to provide an inert base 214 for a layer of RTV. The RTV is screen printed atop the nitride 214 to provide polymer layers 216,218.

A glass or plastic cap 250 cut from a cover wafer and similar to silicon cover 50 in FIG. 2, is fastened to die 240 in FIG. 7. A nitride layer coats both sides of the cover wafer. Nitride openings 244,246 in the backside of the wafer are cut, and a frontside nitride opening 248 is subsequently aligned to backside opening 246 so that when a timed HF etch is completed, a throughhole between openings 246,248 allows liquid, gas or vapor to contact sensor 230. During the same etch, a cavity in the backside of the cover wafer is etched from opening 244. Die 240 and 250 are bonded together using an adhesive such as polyimide or re-flow teflon™ (not shown). The wafers are diced to obtain individual die and a tube port 254 is fastened to the die by a superglue 258. The die is attached to a header 252 by a superglue 258 and tube 254 aligned to an opening in the header.

Figure 8:
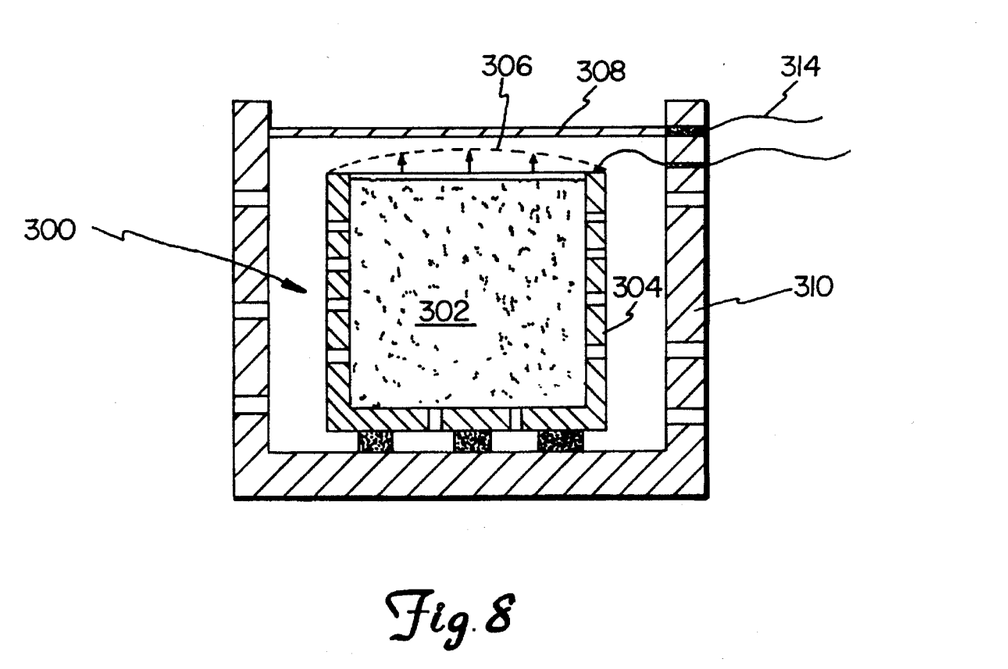
FIG. 8 is a cross section of a fourth embodiment of the invention.

In FIG. 8, an organic chemical sensor 300 includes a polymer 302, which expands in the presence of an organic liquid, gas or vapor, placed in a cylindrical container 304. Container 304 has small diameter holes, on the sides and the bottom, which allow organic chemicals to contact polymer 32. Diaphragm 306 is a bottom capacitor plate and a header cap 308 is an upper capacitor plate. In the presence of an organic, polymer 302 expands in all dimensions but may only move upwards. Such movement exerts an amplified force against a diaphragm 306 so as to deflect it upwards and increase an electrical capacity between the plates. Polymer 302 fills container 304 to a fixed level and conductive diaphragm 306 is laser welded to the upper rim of container 304. Container 304 is fastened into a header 310 and electrical contacts 312,314 are connected to diaphragm 306 and to plate 308, respectively, to monitor capacitance.

Although the present invention has been described with reference to preferred embodiments, workers skilled in the art will recognize that changes may be made in form and detail without departing from the spirit and scope of the invention.

What is claimed is:

1. An organic chemical sensor for sensing at least one of an organic gas, liquid and vapor, comprising:

a container having a deflectable portion;

an electrically non-conductive material disposed in the container, the material exposed to at least one of the organic gas, liquid and vapor and formed of a substance varying a first of its dimensions in the presence of at least one of the organic gas, liquid and vapor so as to deflect the deflectable portion; and a sensor operably coupled at the deflectable portion for detecting deflection and having an output varying as a function of the deflection.

2. The organic chemical sensor of claim 1 wherein the electrically nonconductive material varies a first of its dimensions in the presence of the at least one of the organic gas, liquid and vapor selected from the group consisting of hydrocarbons, chlorohydrocarbons, fluorocarbons and silicarbons.

3. The organic chemical sensor of claim 1 wherein the material is formed of a substance reversibly varying a first of its dimensions in the presence of at least one of the organic gas, liquid and vapor.

4. The organic chemical sensor of claim 1 wherein the container includes a hole allowing at least one of the organic gas, liquid and vapor to contact the material.

5. The organic chemical sensor of claim 4 wherein the container includes a plurality of holes allowing at least one of the organic gas, liquid and vapor to contact the material.

6. The organic chemical sensor of claim 1 wherein the sensor comprises a first capacitor electrode disposed on the deflectable portion and a second capacitor electrode spaced apart from the first capacitor electrode.

7. The organic chemical sensor of claim 1 wherein the material varies only in the first of its dimensions.

* * * * *

UNITED STATES PATENT AND TRADEMARK OFFICE
CERTIFICATE OF CORRECTION

PATENT NO. : 5,482,678
DATED : January 9, 1996
INVENTOR(S) : Fred C. Sittler

It is certified that error appears in the above-indentified patent and that said Letters Patent is hereby corrected as shown below:

Title page, page 2

[56]  References Cited

U.S. PATENT DOCUMENTS

Reference No. 9  --  3,460,378  8/1969
replace "Gepollina" with --Cepollina--.

Signed and Sealed this

Thirtieth Day of July, 1996

Attest:

BRUCE LEHMAN

*Attesting Officer*  *Commissioner of Patents and Trademarks*